(12) United States Patent
Lorenzo et al.

(10) Patent No.: US 10,939,917 B2
(45) Date of Patent: Mar. 9, 2021

(54) EXPANDABLE VASCULAR OCCLUSION DEVICE WITH LEAD FRAMING COIL

(71) Applicant: DePuy Synthes Products, Inc., Raynham, MA (US)

(72) Inventors: Juan Lorenzo, Raynham, MA (US); Hussein Girnary, Raynham, MA (US); Robert Slazas, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 219 days.

(21) Appl. No.: 16/122,117

(22) Filed: Sep. 5, 2018

(65) Prior Publication Data
US 2019/0000485 A1 Jan. 3, 2019

Related U.S. Application Data

(62) Division of application No. 14/701,695, filed on May 1, 2015, now Pat. No. 10,111,670.

(51) Int. Cl.
*A61B 17/12* (2006.01)
*A61F 2/06* (2013.01)

(52) U.S. Cl.
CPC .... *A61B 17/12118* (2013.01); *A61B 17/1214* (2013.01); *A61B 17/12022* (2013.01);
(Continued)

(58) Field of Classification Search
CPC .... A61F 2/01; A61F 2/06; A61F 2/013; A61F 2/062; A61F 2002/011; A61B 17/12;
(Continued)

(56) References Cited

U.S. PATENT DOCUMENTS

| 5,536,274 A | 7/1996 | Neuss |
| 5,911,731 A | 6/1999 | Pham et al. |

(Continued)

FOREIGN PATENT DOCUMENTS

| CN | 102302377 A | 1/2012 |
| CN | 104411256 A | 3/2015 |

(Continued)

OTHER PUBLICATIONS

Turk et al. "Periprocedural safety of aneurysm embolization with the Medina Coil System: the early human experience" J NeuroIntervent Surg 0:1-5 (2015).

(Continued)

*Primary Examiner* — Vi X Nguyen
(74) *Attorney, Agent, or Firm* — Troutman Pepper Hamilton Sanders LLP

(57) ABSTRACT

A method of treating an aneurysm with an occlusion device having an inner embolic device with a proximal section and a distal section. The distal section has a first stiffness and the proximal section has a second stiffness. Further, the device has an expandable mesh capable of a collapsed position and an expanded position. The mesh can be disposed over, and attached to, a portion of the proximal section of the inner embolic device. The first stiffness is greater than the second stiffness and the inner embolic device comprises a preselected shape which assists in transforming the expandable mesh from the collapsed position to the expanded position.

9 Claims, 18 Drawing Sheets

(52) U.S. Cl.
CPC .. *A61B 17/12031* (2013.01); *A61B 17/12113* (2013.01); *A61B 17/12145* (2013.01); *A61B 17/12168* (2013.01); *A61B 17/12172* (2013.01); *A61F 2/062* (2013.01); *A61B 2017/1205* (2013.01); *A61F 2002/068* (2013.01); *A61F 2230/0069* (2013.01)

(58) Field of Classification Search
CPC .......... A61B 17/12118; A61B 17/1214; A61B 17/12022; A61B 17/12031; A61B 17/12113; A61B 17/12145; A61B 17/12168

See application file for complete search history.

(56) References Cited

U.S. PATENT DOCUMENTS

| | | | |
|---|---|---|---|
| 6,019,779 | A | 2/2000 | Thorud et al. |
| 6,063,111 | A | 5/2000 | Hieshima et al. |
| 6,280,457 | B1 | 8/2001 | Wallace et al. |
| 6,425,915 | B1 | 7/2002 | Khosravi et al. |
| 6,494,907 | B1 | 12/2002 | Bulver |
| 8,361,104 | B2 | 1/2013 | Jones et al. |
| 8,444,668 | B2 * | 5/2013 | Jones ................. A61B 17/1214 606/200 |
| 8,974,512 | B2 | 3/2015 | Aboytes et al. |
| 8,998,947 | B2 | 4/2015 | Aboytes et al. |
| 2008/0032745 | A1 | 2/2008 | Kim et al. |
| 2008/0097508 | A1 | 4/2008 | Jones et al. |
| 2008/0195139 | A1 | 8/2008 | Donald et al. |
| 2012/0065660 | A1 * | 3/2012 | Ferrera ..................... A61F 2/95 606/198 |
| 2012/0239074 | A1 | 9/2012 | Aboytes et al. |
| 2013/0066357 | A1 | 3/2013 | Aboytes et al. |
| 2013/0116722 | A1 | 5/2013 | Aboytes et al. |
| 2013/0253572 | A1 | 9/2013 | Molaei et al. |
| 2015/0272590 | A1 | 10/2015 | Aboytes et al. |

FOREIGN PATENT DOCUMENTS

| | | |
|---|---|---|
| JP | 2014-525806 A1 | 10/2014 |
| WO | 9915116 A1 | 4/1999 |
| WO | 2006/034149 A2 | 3/2006 |
| WO | WO2010/123003 A1 | 10/2010 |
| WO | 2012/034135 A1 | 3/2012 |
| WO | 2013/138615 A2 | 9/2013 |
| WO | 2013/142756 A1 | 9/2013 |

OTHER PUBLICATIONS

Extended European Search Report dated Sep. 26, 2016 issued in corresponding European Patent Application No. 16167752.1.
Notification of Reasons for Refusal issued in corresponding Japanese Patent Application No. 2016-090754 dated Feb. 18, 2020, with English translation.
Chinese Office Action issued in corresponding Chinese Patent Application No. 201610286145.1 dated Mar. 20, 2020 (document in Chinese ).

* cited by examiner

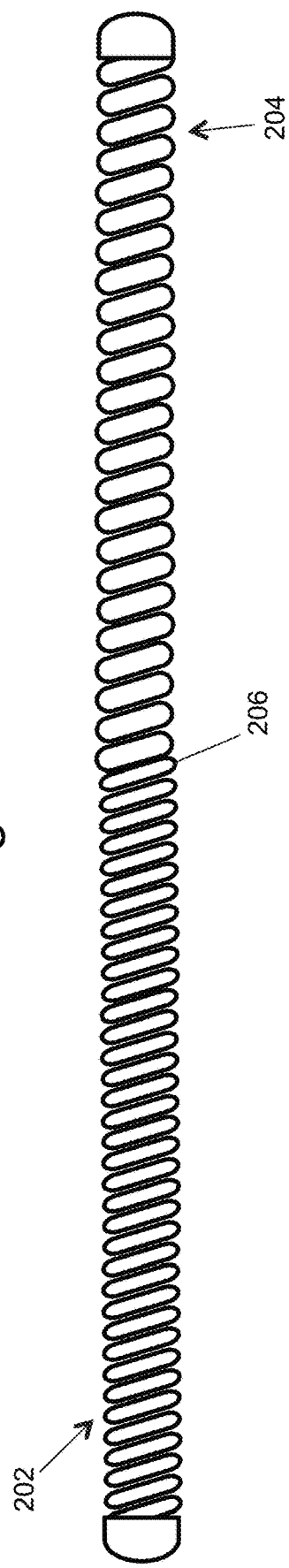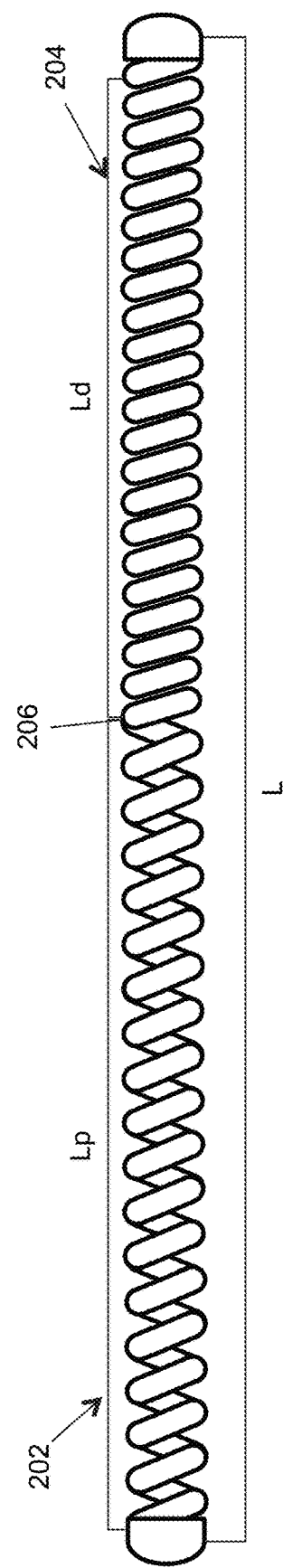
Figure 6
Figure 7

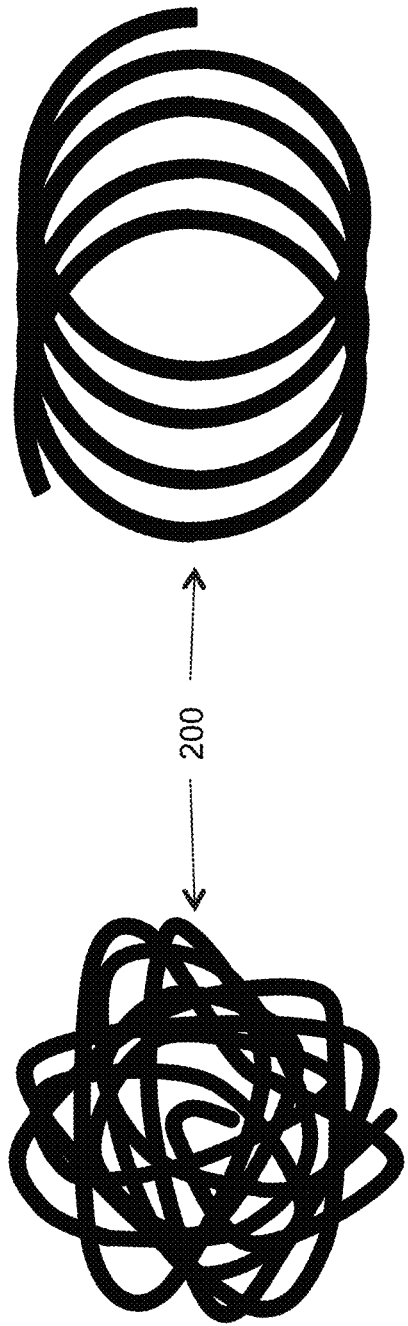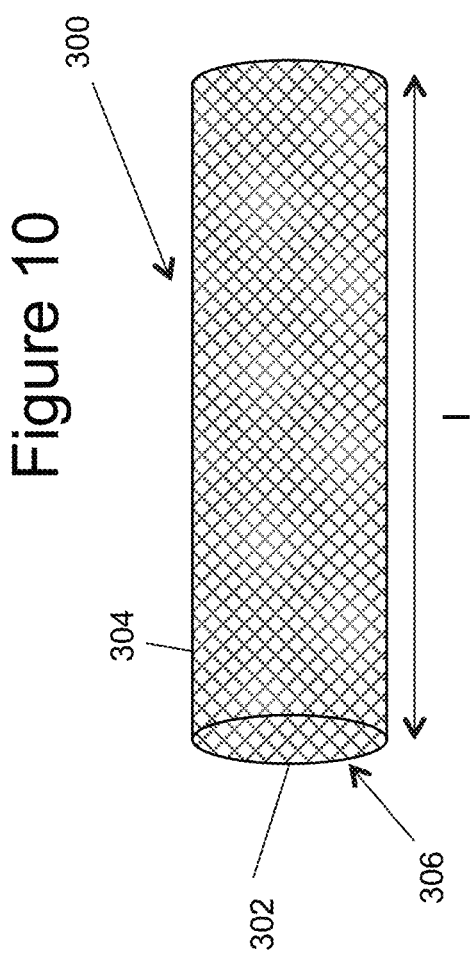

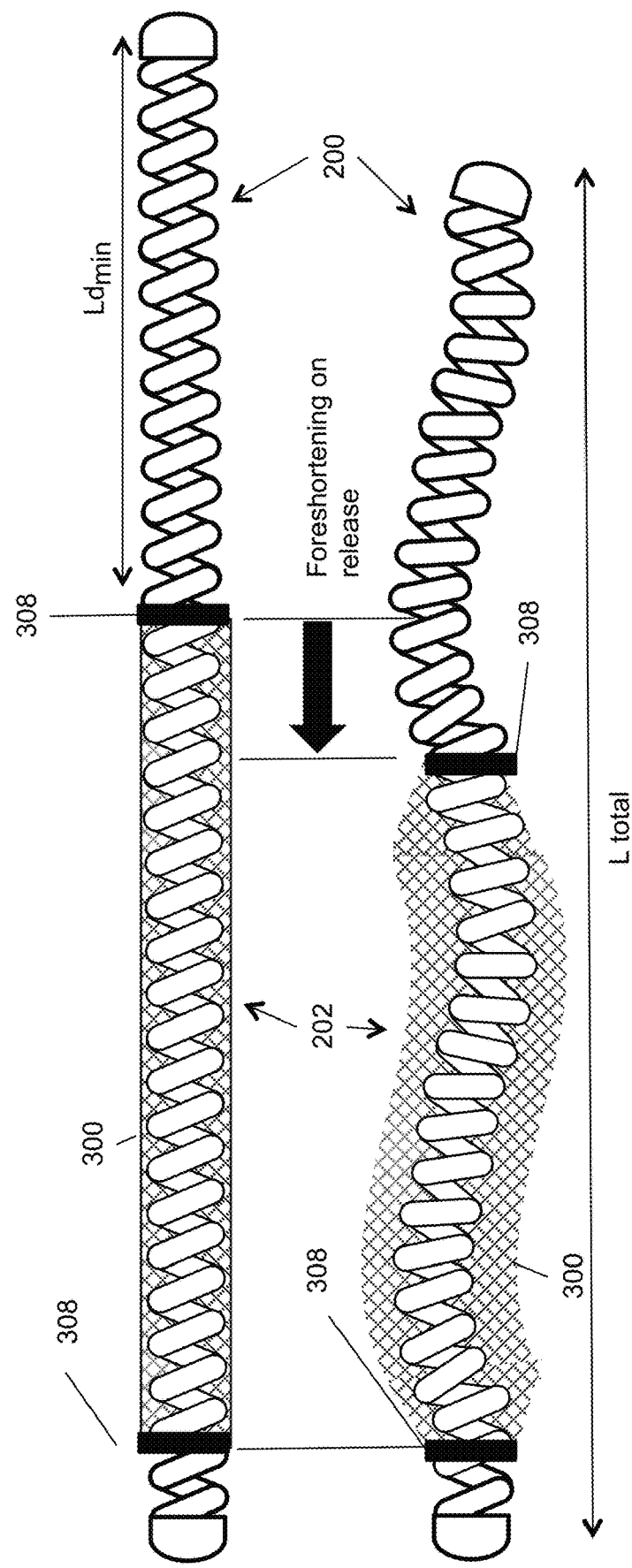

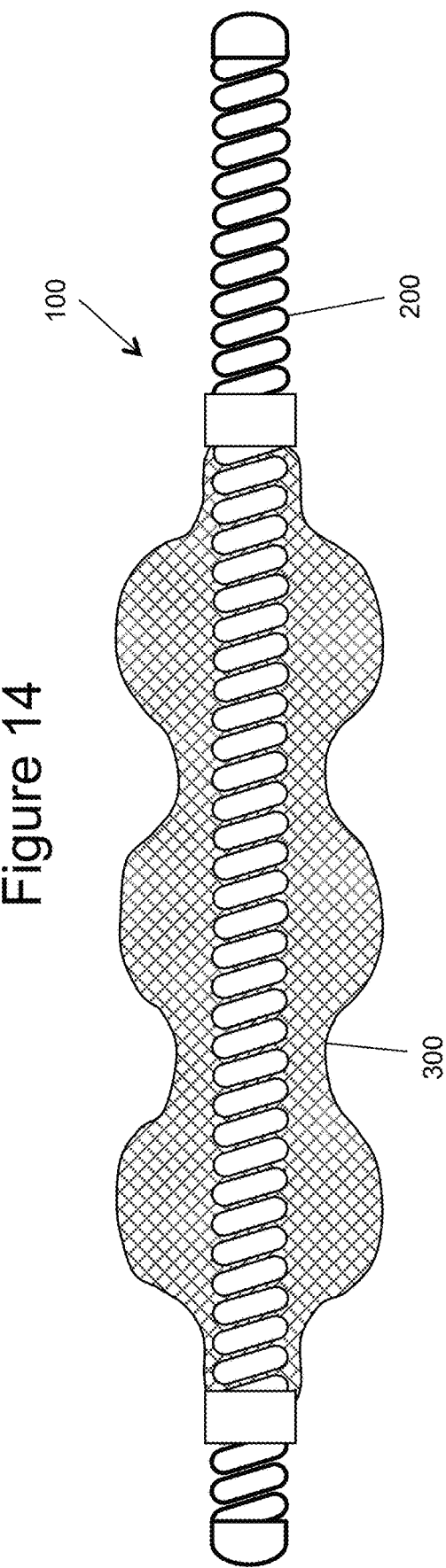
Figure 14
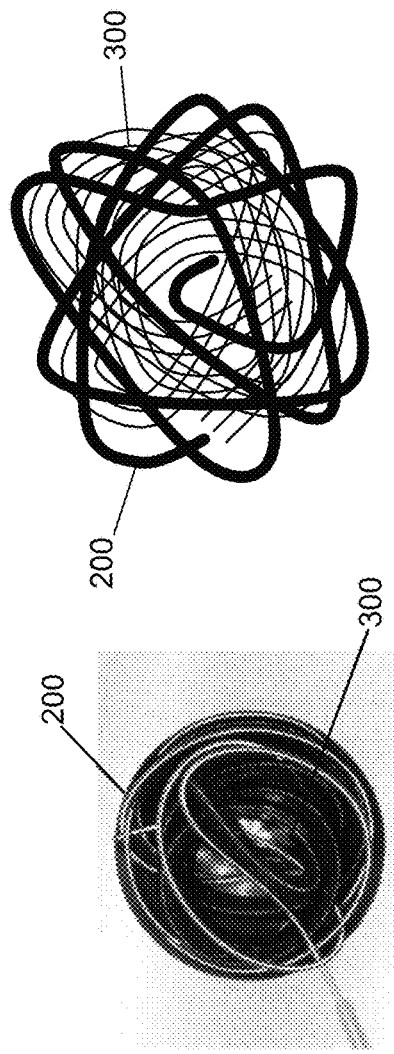
Figure 16B
Figure 16A
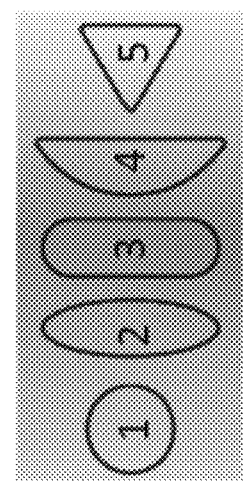
Figure 15

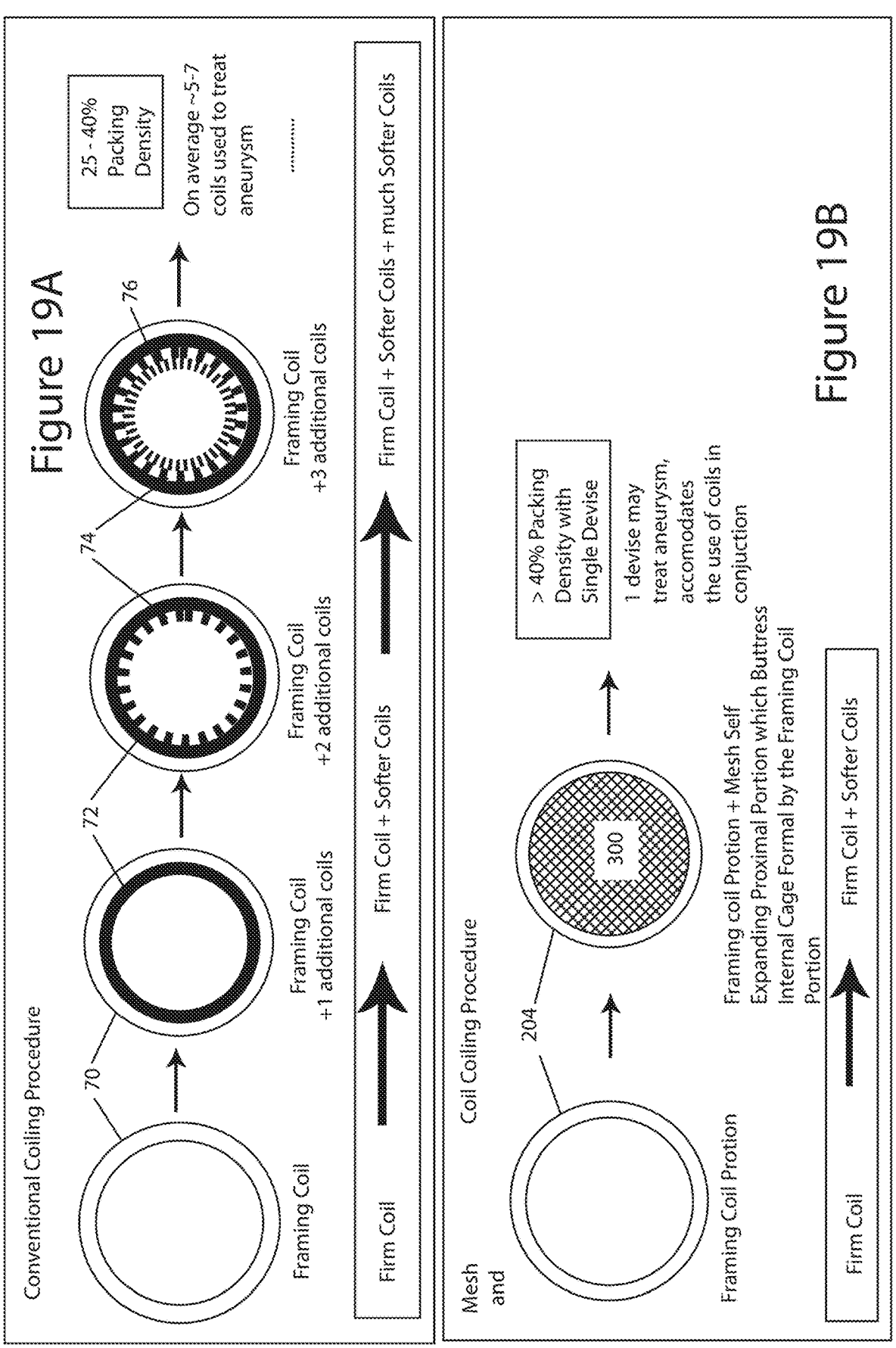

Framing portion of inner embolic coil

Mesh portion of inner embolic coil

Figure 21

| Aneurysm Size (mm) | 4 | 4 | 14 | 14 | 24 | 24 | 34 | 34 |
|---|---|---|---|---|---|---|---|---|
| Aneurysm Volume (mm^3) | 33.5 | 33.5 | 1436.7 | 1436.7 | 7238.2 | 7238.2 | 20579.5 | 20579.5 |
| Distal Coil Diameter (mm) | 0.635 | 0.2032 | 0.635 | 0.2032 | 0.635 | 0.2032 | 0.635 | 0.2032 |
| Frame with Coil (Spherical Shell) volume (mm^3) | 22.9 | 9.2 | 356.6 | 121.5 | 1089.3 | 361.5 | 2221.0 | 729.2 |
| Pack with Mesh (Hollow Sphere) Volume (mm^3) | 10.7 | 24.3 | 1080.1 | 1315.2 | 6148.9 | 6876.7 | 18358.5 | 19850.4 |
| Length Coil (mm) – assuming 100% PD | 72.2 | 284.0 | 1126.0 | 3747.4 | 3439.7 | 11147.7 | 7013.3 | 22485.0 |
| Length Mesh (mm) assuming 1mm Diameter Mesh and 100% PD | 13.6 | 30.9 | 1375.3 | 1674.6 | 7829.0 | 8755.7 | 23374.7 | 25274.3 |
| Length Mesh (mm) assuming 2mm Diameter Mesh and 100% PD | 3.4 | 7.7 | 343.8 | 418.7 | 1957.3 | 2188.9 | 5843.7 | 6318.6 |
| Ratio Length Coil: Device Length (assuming 1mm Diameter Mesh and PD Mesh = 1x PD Coil) | 84.2% | 90.2% | 45.0% | 69.1% | 30.5% | 56.0% | 23.1% | 47.1% |
| Ratio Length Coil: Device Length (assuming 2mm Diameter Mesh and PD Mesh = 1x PD Coil) | 95.5% | 97.3% | 76.6% | 90.0% | 63.7% | 83.6% | 54.5% | 78.1% |
| Ratio Length Coil: Device Length (assuming 1mm Diameter Mesh and PD Mesh = 2x PD Coil) | 72.7% | 82.1% | 29.0% | 52.8% | 18.0% | 38.9% | 13.0% | 30.8% |
| Ratio Length Coil: Device Length (assuming 2mm Diameter Mesh and PD Mesh = 2x PD Coil) | 91.4% | 94.8% | 62.1% | 81.7% | 46.8% | 71.8% | 37.5% | 64.0% |
| Ratio Length Coil: Device Length (assuming 1mm Diameter Mesh and PD Mesh = 4x PD Coil) | 57.1% | 69.7% | 17.0% | 35.9% | 9.9% | 24.1% | 7.0% | 18.2% |
| Ratio Length Coil: Device Length (assuming 2mm Diameter Mesh and PD Mesh = 4x PD Coil) | 84.2% | 90.2% | 45.0% | 69.1% | 30.5% | 56.0% | 23.1% | 47.1% |

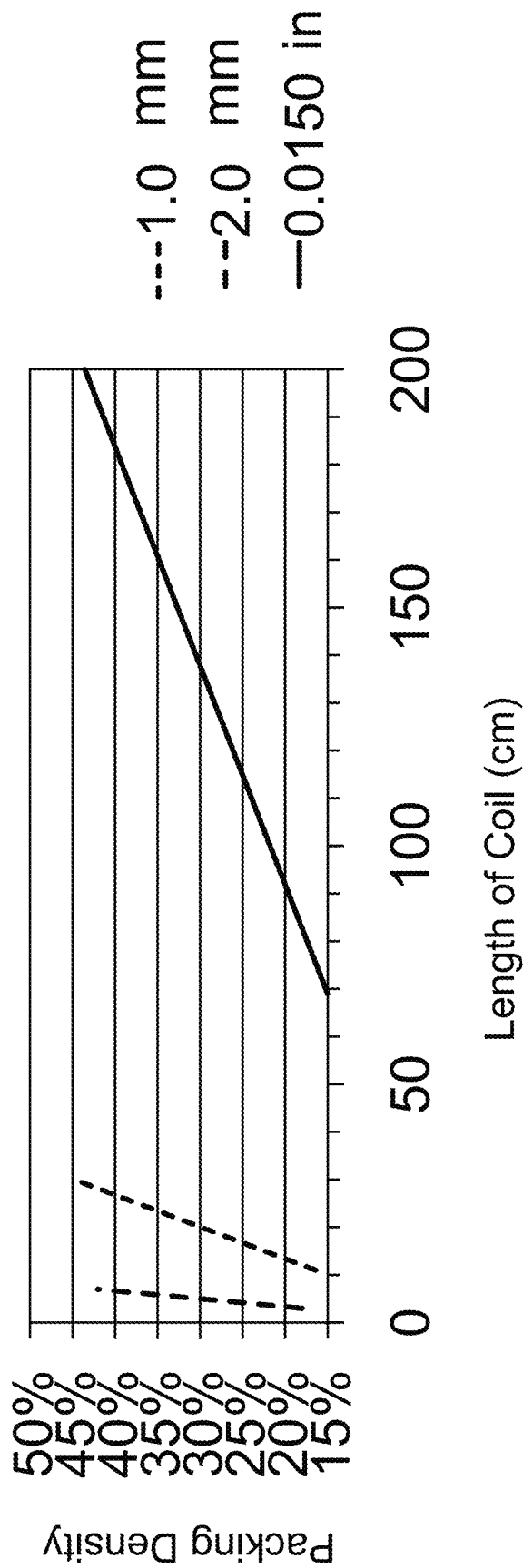

EXPANDABLE VASCULAR OCCLUSION DEVICE WITH LEAD FRAMING COIL

CROSS-REFERENCE TO RELATED APPLICATIONS

This application is a Divisional Application of U.S. application Ser. No. 14/701,695 filed on May 1, 2015, all of which applications are herein incorporated by reference in their entirety.

FIELD OF THE INVENTION

The present invention generally relates to medical devices and methods which are used to occlude vessels within a patient, and more particularly, to occlusion devices which include an expandable mesh.

BACKGROUND

An aneurysm is an abnormal bulge or ballooning of the wall of a blood vessel. Typically, an aneurysm develops in a weakened wall of an arterial blood vessel. The force of the blood pressure against the weakened wall causes the wall to abnormally bulge or balloon outwardly. One detrimental effect of an aneurysm is that the aneurysm may apply undesired pressure to tissue surrounding the blood vessel. This pressure can be extremely problematic especially in the case of a cranial aneurysm where the aneurysm can apply pressure against sensitive brain tissue. Additionally, there is also the possibility that the aneurysm may rupture or burst leading to more serious medical complications including mortality.

When a patient is diagnosed with an unruptured aneurysm, the aneurysm is treated in an attempt to reduce or lessen the bulging and to prevent the aneurysm from rupturing. Unruptured aneurysms have traditionally been treated by what is commonly known in the art as "clipping." Clipping requires an invasive surgical procedure wherein the surgeon makes incisions into the patient's body to access the blood vessel containing an aneurysm. Once the surgeon has accessed the aneurysm, a clip is placed around the neck of the aneurysm to block the flow of blood into the aneurysm and prevents the aneurysm from rupturing. While clipping may be an acceptable treatment for some aneurysms, there is a considerable amount of risk involved with employing the clipping procedure for treating certain types of cranial aneurysms because such procedures generally require open brain surgery and the location of the aneurysm can pose risks and may even prevent using this kind of procedure.

Intravascular catheter techniques have been used to treat cranial aneurysms, and are generally more desirable because such techniques do not require cranial or skull incisions, i.e., these techniques do not require open brain surgery. Typically, these techniques involve using a catheter to deliver an occlusion device (e.g., embolic coils) to a preselected location within the vasculature of a patient. For example, in the case of a cranial aneurysm, methods and procedures which are well known in the art are used for inserting and guiding the distal end of a delivery catheter into the vasculature of a patient to the site of the cranial aneurysm. A vascular occlusion device which is generally attached to the end of a delivery member is then traversed through to the delivery catheter until the occlusion is delivered into the aneurysm. The methods for delivering an occlusion device in a catheter are well known to those of skill in the art.

Once the occlusion device has been delivered to and deployed into the aneurysm, the blood within the aneurysm will generally clot in and around the occlusion device to form a thrombus. The thrombus that forms seals off the aneurysm so that blood from the surrounding vessels no longer flows into the aneurysm, this prevents further ballooning or rupture. The deployment procedure is repeated until the desired number of occlusion devices are deployed within the aneurysm. Typically, it is desired to deploy enough coils to obtain a packing density of about 20% or more, preferably about 35% and more if possible.

The most common vascular occlusion device is an embolic coil. Embolic coils are typically constructed from a metal wire which may be wound into a variety of shapes, including a helical shape. As explained above, a procedure may require using numerous embolic coils so that there is a large enough surface area for blood to clot thereto. Sometimes the embolic coil may be situated in such a way within an aneurysm that there are relatively considerable gaps between adjacent coils which can allow blood to freely flow into and within the aneurysm. The addition of extra coils into the aneurysm does not always solve this problem because deploying too many coils into the aneurysm may lead to an undesired rupture.

Another technique is to use meshes, similar to stents, to fill the aneurysm. The benefit to these devices is that they can expand many times the diameter needed to deliver the mesh through the catheter. This allows for a smaller length of mesh, in comparison to embolic coils, needed to achieve packing densities above 35%. The smaller length is dictated by the fact that the mesh can expand and thus occupy more space within the aneurysm even though it has a shorter length. By contrast, to achieve this same result, more (or longer lengths of) embolic coils are needed since they retain their diameter to fill the same void. FIG. 22 illustrates an example of a packing density comparison between a 1 mm outer diameter (OD) mesh, a 2 mm OD mesh and a 0.0150 inch (0.381 mm) OD embolic coil. In a 10 mm spherical aneurysm, an approximately 45% packing density is achieved with approximately a 7.5 cm length of the 2 mm mesh, an approximately 45% packing density is achieved with approximately 30 cm of 1 mm mesh and more than a 200 cm length of the embolic coil (at 0.015 in) is needed for an approximately 45% packing density.

This example highlights some of the challenges with mesh and embolic coils. For the mesh, there may not be sufficient length of the mesh in the aneurysm before density is reached. This leaves the mesh unsupported and can lead to compaction. Compaction is as it sounds, the mesh is compressed by blood flow into and past the aneurysm, and that decreases the portion of aneurysm treated by the mesh. Sometimes the portion treated is decreased below the point of being effective and a second procedure is needed to refill the aneurysm to get a sufficient packing density. For the embolic coil, they are typically much shorter than 200 cm and, as explained, multiple coils must be deployed into the aneurysm to reach an acceptable packing density, this increases the surgery time as each embolic coil must be advanced through the catheter.

Therefore, there remains for a better occlusion device that provides a greater occupied volume to promote the clotting of blood and decrease surgery time. The present invention presents such kinds of devices. Further, if multiple devices are used, the occlusion devices of the present invention can also effectively occupy the space between adjacent occlusion devices without increasing the risk of rupturing the aneurysm.

SUMMARY

Disclosed herein are various exemplary devices of the present invention that can address the above needs, which devices generally include an inner embolic device with a proximal section and a distal section, and may also include an expandable mesh. In this manner, the devices of the invention permit for one device to be used thereby minimizing surgical time, and achieving greater packing density using, for example, smaller lengths of devices and less devices.

In this context, the proximal section of the inner embolic device is the end closest to the physician and the distal section is the section farthest away from the physician. The distal section can have a first stiffness and the proximal section can have a second stiffness. The occlusion device can also include an expandable mesh capable of being transformed between a collapsed position and an expanded position. The expandable mesh can be disposed over, and attached to, a portion of the proximal section of the inner embolic device. The first stiffness of the inner embolic device can be greater than the second stiffness. Further, the inner embolic device can have a preselected shape which assists in transforming the expandable mesh from the collapsed position to the expanded position.

Another example of the inventive occlusion devices includes an expandable mesh covering substantially the entire proximal section of the inner embolic device. Also, the expandable mesh can have a preselected shape that it takes when transformed from the collapsed position to the expanded position. That preselected shape of the expandable mesh can assist in the transformation from the collapsed position to the expanded position. Further, the inner embolic device can also have a preselected shape at both its proximal and distal sections.

Further examples of the inventive occlusion devices include the inner embolic device having a transition zone between the first stiffness and second stiffness. The first stiffness can be up to approximately ten times the second stiffness. Also, the occlusion devices can have a proximal section and a distal section that are of varying lengths. For example, a length of the distal section may be at least approximately 7% of the total length of the device. Here, the lengths of the proximal section and the distal section can be equal, or one greater than the other. In another example, the length of the proximal section is substantially longer than the distal section.

An example method of treating an aneurysm using an example of an occlusion device of the claimed invention can have the steps of configuring the different stiffness of the inner embolic element so that the distal section is stiffer than the proximal section. The stiffer distal section can also be referred to as a framing coil. By this, as explained in more detail below, the distal section "frames" the aneurysm so the proximal section that includes a mesh, can "fill in" the aneurysm to reach the proper packing density, as discussed above.

An occlusion device of the invention can be placed within a vessel of a patient and can be directed to the aneurysm. Once there, the distal section/framing coil of the inner embolic element is deployed into the aneurysm, allowing it to take a predetermined shape (e.g., a shape determined in advance). This shape, as noted above, can "frame" the aneurysm. Once the distal section is in place, the remaining portion of the occlusion device is advanced. This deploys the expandable mesh, with the proximal section of the inner embolic element, into the aneurysm. The mesh can then self-expand into its predetermined shape, filling the aneurysm to attain a packing density that is greater than that of the embolic coil alone.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIGS. 3-7 illustrate different examples of an inner embolic element (e.g. a framing coil once deployed, and a proximal section);

FIG. 8 illustrates a 3-D complex configuration of an inner embolic element;

FIG. 9 illustrates an approximately 2-D simple helical configuration of an inner embolic element;

FIG. 10 illustrates a side view of a self-expandable mesh;

FIGS. 12a and 12b illustrate an example of a vascular occlusion device where the coil can shape the mesh on deployment;

FIG. 14 illustrates a mesh in an example of a non-uniform configuration;

FIG. 15 illustrates different examples of cross-sections for a mesh;

FIGS. 16a and 16b illustrate 3-D complex configurations of an embolic device, as deployed;

FIGS. 19a and 19b illustrate a cross-sectional simplified comparison between the prior art and an example of the present invention;

FIG. 21 is a table illustrating examples of packing densities and length ratios for the vascular occlusion device; and FIG. 22 is a graph comparing the packing densities of prior art coils and meshes.

DETAILED DESCRIPTION

Figure 1:
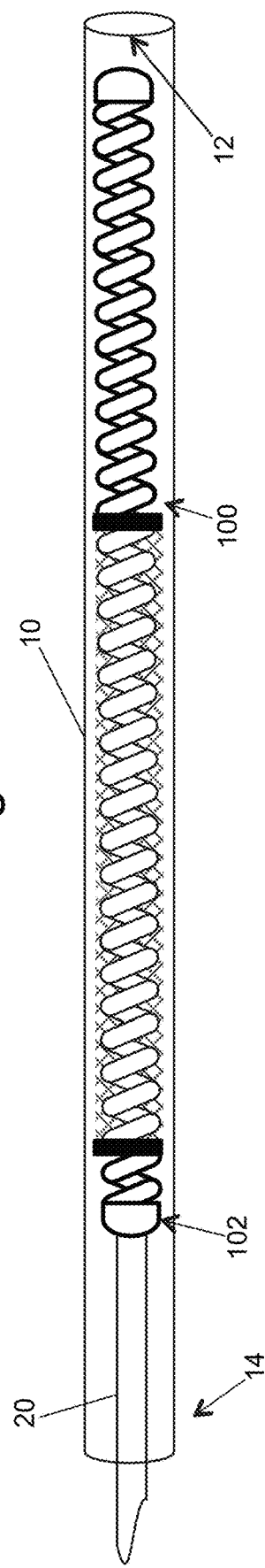
FIG. 1 is a side view of an exemplary vascular occlusion device of the present invention inside a catheter.

FIG. 1 generally illustrates an example of a vascular occlusion device 100 within a delivery catheter 10 and connected to a vascular occlusion delivery system 20. The catheter is a typical catheter used for neurovascular procedures. The catheter size is selected in consideration of the size, shape, and directionality of the aneurysm or the body lumens the catheter must pass through to get to the treatment site. The catheter 10 may have a total usable length anywhere from 80 centimeters to 165 centimeters and a distal length of anywhere between 5 centimeters to 42 centimeters. The catheter 10 may have an inner diameter (ID) of anywhere between 0.010 and 0.030 inches. The outer diameter (OD) may also range in size and may narrow at either its proximal section or distal section. The outer diameter may be 3 French or less. For the below examples, the proximal section of an inner embolic device is the end closet to the physician and the distal section is farthest away from the physician.

An occlusion device 100 typically exits the distal section 12 of the catheter 10 to be deployed into an aneurysm 50. A proximal section 14 of the catheter 10 can house the delivery system 20. The delivery system 20 is typically removeably connected to a proximal section 102 of the occlusion device 100 to deploy and/or retrieve the occlusion device 100 out of the catheter 10 and into the aneurysm 50. Delivery systems 20 are known to those of skill in the art and any can be used with any example of the present invention to deploy and/or retrieve coils, meshes, or other devices. Delivery systems 20 may include pusher members with any of the known mechanisms to release the vascular occlusion device 100, which can include mechanical, electrical, hydraulic, or thermal mechanisms. In some examples, the vascular occlusion device 100 is pushed out of the catheter 10 and into the aneurysm 50, as opposed to placing the catheter 10 and device 100 in the aneurysm 50 and removing the catheter 10.

Figure 2:
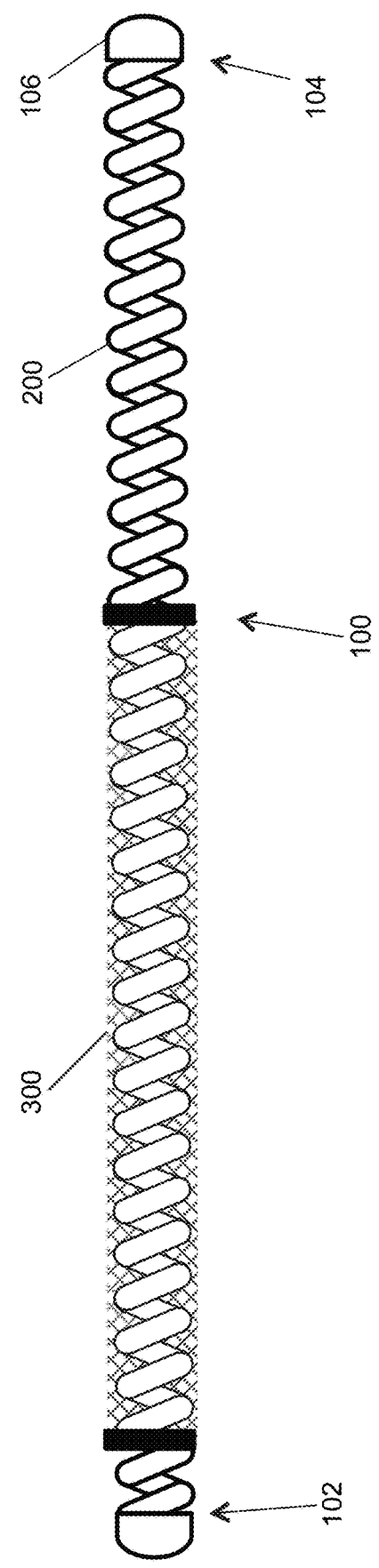
FIG. 2 is a view of an example of a vascular occlusion device of the present invention.

Turning now to an example of the occlusion device 100, as illustrated in FIG. 2, it has proximal 102 and distal 104 sections. The distal section 104 can have an atraumatic tip 106, for example in the form of a weld, or solder bead and is thus designed to not cause any damage or injury to tissues when advancing through a body orifice. The occlusion device 100 can have two main parts, an inner embolic element 200 and a self-expanding mesh 300.

The inner embolic element 200 can act as a standard embolic coil. FIGS. 3-7 illustrate different examples of the inner embolic element 200. The inner embolic element 200 can have a proximal section 202 and a distal section 204 and in some instances a transition zone 206. The inner embolic element 200 can act as a standard embolic coil, it may be relatively stiff or it may be relatively soft. The inner embolic element 200 may be made with any biocompatible materials commonly used in the art such as nickel-titanium alloy, cobalt chromium alloys, Platinum, Nitinol, Stainless Steel, Tantalum, or other alloys; or any other suitable biocompatible materials, or combination of these materials. The stiffness of the inner embolic element 200 can be adjusted by, for example, typical coil parameters of coil wire diameter, coil wound diameter, coil pitch, and coil material. In the instance of a coil, the diameter of the coil is selected in consideration of the size and shape of the aneurismal sac, which can be a variety of shapes and sizes. The inner embolic element 200 may come in various random loop designs to conform to the aneurysm shape (discussed below). The number of loops, or turns, in a coil may also vary. Platinum coils may be between about 0.008 inches and 0.025 inches in diameter. A coil may vary from about 1 to 60 centimeters in length, with some as long as 100 centimeters. The inner embolic element 200 can also be made of a radiopaque material such as platinum or tungsten to provide radiopacity, which aids in the delivery of the occlusion device 100.

Figure 3:
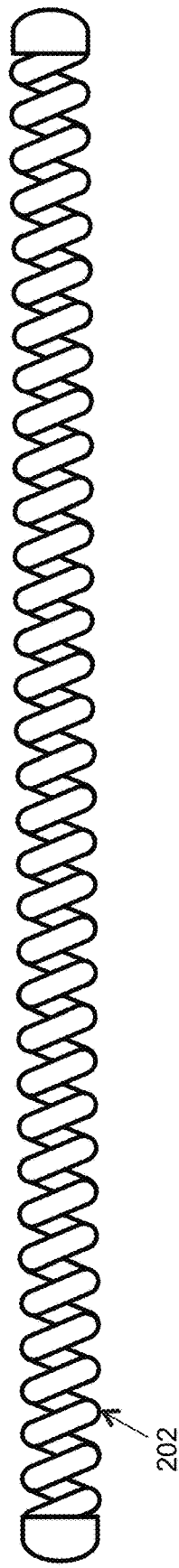
Figure 4:
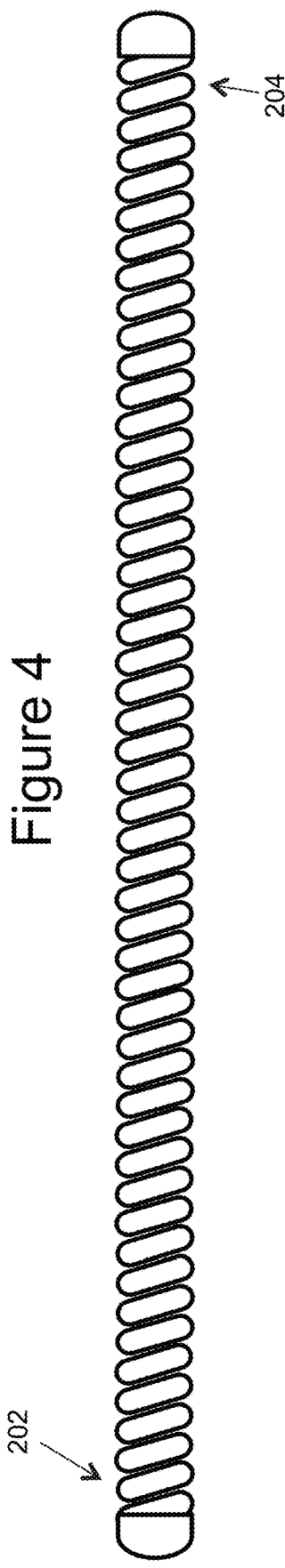
Figure 5:
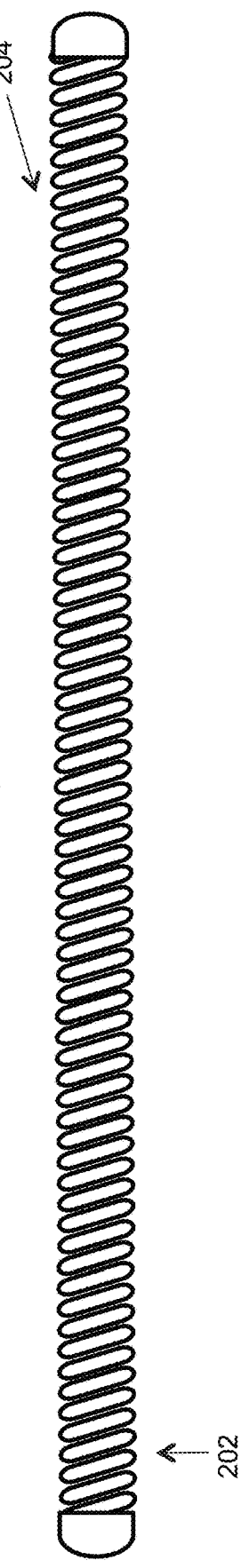

A coil can vary along its length in softness and in stiffness. FIGS. 3-5 illustrate different examples used to change the stiffness of the inner embolic element 200. This can be by opening the coil pitch (FIG. 3), increasing the coil diameter (FIG. 4), or using a smaller wire (FIG. 5). Additionally, a coil can be annealed in sections to soften the metal. FIGS. 6 and 7 illustrate another way of varying stiffness which is a single inner embolic element 200 having a varying stiffness along its length. In the figures, a transition zone 206 illustrates where the stiffness changes between the distal section 204 and the proximal section 202, and the distal section 204 is stiffer than the proximal section 202. Note other examples may have multiple transitions zones where the stiffness may change numerous times when moving along the total length L.

In general proportions, the stiff distal section 204 of the inner embolic element 204 is typically greater than or equal to 5% of the total length L of the entire inner embolic element 200. In other examples, the stiff distal section 204 can be between approximately 20 to 30 times the stiffness of the proximal section 202. Thus, the stiffness of the distal section 204 can be considered a first stiffness while the stiffness of the proximal section 202 can be a second stiffness. In FIG. 7, there can be a length of the distal section Ld and a length of the proximal section Lp that have different stiffness. In examples, the ratio of the length of the distal section Ld and the length of the proximal section Lp are discussed below.

In another example of the inner embolic element 200, all or part of the element 200 can be configured to form simple or complex predetermined configurations or shapes once deployed from the catheter 10. FIGS. 8 and 9 illustrate examples of different configurations. FIG. 8 illustrates a complex, random three-dimensional shape, while FIG. 9 illustrates a simple two-dimensional helical shape. In another example, the distal section of the inner embolic element 200 may take a configuration suitable for framing the aneurysm. This "framing coil" portion is shaped to expand to the near periphery of the aneurysm. The portion of the inner embolic element between the two ends of the self-expanding mesh 300 may take different configurations, e.g. one suitable for accommodating the difference in length of the self-expanding mesh 300 between the constrained and deployed state. The inner embolic element may consist of a single continuous coil or multiple sections of similar or different coils or other suitable devices joined together e.g. by welding, soldering, crimping or other suitable method.

In one example, the proximal section 202, as identified by its length Lp in FIG. 7, and the distal section 204, as identified by its length Ld in FIG. 7, can take different configurations over the total length L, at least based on their stiffness. In one example, when in the catheter 10, the portion of the inner embolic element 200 between the two ends of the self-expanding mesh can be under compression and this applies a tensile force to axially or radially stretch out the self-expanding mesh 300, as in FIG. 11. Placing the mesh 300 in tension allows it to adopt its longest length and smallest diameter (i.e. a collapsed state), this profile reduces frictional forces during delivery of the device. The compressed portion of the inner embolic element reverts to its natural pre-formed state upon deployment of the device from the catheter 10. Designing the inner embolic element 200 to be in compression when in the catheter can be by the use of different length wires to form the coils. A further design can be achieved during attachment of the mesh 300 to all or part of the proximal section of the coil. A slightly shorter mesh 300 (in the constrained state in the catheter) than the length of the coil between is attached to the coil so when the coil is straight inside the catheter 10, the mesh 300 is in tension and in its collapsed state.

FIG. 10 illustrates a self-expanding mesh 300 which can be comprised of a tube of mesh made of several materials such as deposited thin films. The self expanding mesh 300 can include multiple wires, for example from 4 to 96 wires, and be made from multiple alloys such as a nickel-titanium alloy, cobalt chromium alloys, Platinum, Nitinol, Stainless Steel, Tantalum, or other alloys, or any other suitable biocompatible materials, or combination of these materials. Also, these materials can be absorbable or non-absorbable by the patient over time. Additionally, although the self-expanding mesh 300 is illustrated as generally cylindrically shaped, it is contemplated that the generally tubular element could also be in the form of different shapes, for example, an elongated generally cubical shape, discussed further below.

The apertures 304 in the mesh 300 create a substantially unitary frame work or mesh in the wall 302. Thus, the apertures 304 may be of any size, shape, or porosity, and may be uniformly or randomly spaced throughout the wall 302 of the mesh 300. The apertures 304 provide the tubular element with flexibility and also assist in the transformation of the mesh 300 from the collapsed state to the expanded state, and vice versa.

Figure 11:
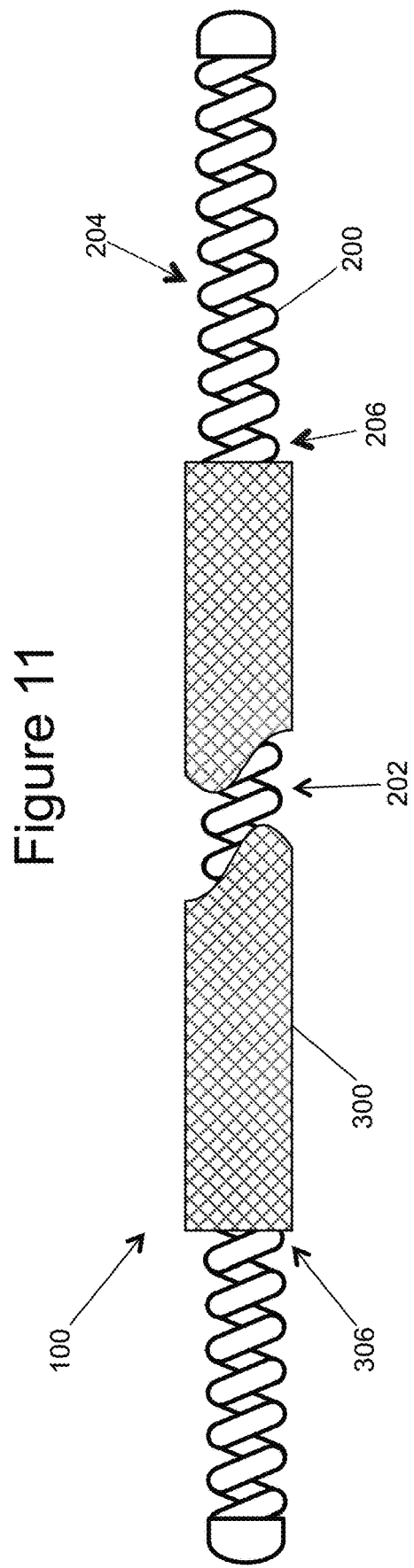
FIG. 11 illustrates a partially cut-away side view of an inner embolic element and the mesh, as assembled.

The occlusion device 100, as noted above, can include the assembly of the inner embolic coil 200 and the mesh 300. In an example, to assemble, the inner embolic element 200 is inserted into an opening 306 located at either end of the mesh 300 so that the mesh 300 covers at least a portion of the inner embolic element 200. As illustrated in FIG. 11, the mesh 300 may cover substantially the entire proximal section 202, part of the proximal section 202, or the middle of the proximal section 202 of inner embolic element 200, leaving at least the distal section 204 uncovered. The mesh 300 can then be attached (not shown) to the inner embolic element 200 by friction fit, biocompatible adhesives, solder, welding, crimping or other approach suitable for use in the body. In examples, the mesh 300 can be connected to the inner embolic element 200 in any number of places.

In one example, the mesh 300 covers a softer portion of the inner embolic element (coil) 200, for example, typically the proximal section 202 of the coil 200. Thus, one end of the mesh 300 can be attached at or near the transition zone 206. In examples, the distal section 204 of the coil 200 is longer than the proximal section 202, based on the transition zone 206. This is also true for the mesh 300, it can be typically shorter in length than the proximal section length Lp of the coil 200, and, in other examples, it can be shorter than 17%, 34%, or 50% of the proximal section length Lp. In another example, the length of the mesh 300 can be approximately equal to the entire proximal section length Lp of the inner embolic element 200. The examples can include the length Lp slightly longer than the mesh 300 when the mesh 300 is in the collapsed state. In one example, proximal section length Lp is approximately 2-5% longer than the length l, or 1.02 l to 1.05 l≈Lp. Further, the length of the mesh in its expanded position is typically less than the length l (i.e. when in the collapsed position).

As another example, take the deployed length, which is the entire length L and subtract out a minimal length of the distal section $Ld_{min}$. This $Ld_{min}$ can be approximately 7% of total device length L. The length of the inner embolic device 200 under the mesh (the proximal portion in some examples) can be dependent on how much the mesh 300 foreshortens when the inner embolic element 200 also shortens. This leads to a range of length options. For this example, if the constrained mesh length l is no more than approximately 150% of unconstrained mesh length, then the ration of the stiff distal section 204 of the inner embolic element 200 is approximately 5% of the total length L of the entire inner embolic element 200.

FIGS. 12a and 12b illustrate another example of assembling the mesh 300 to the inner embolic element 200. Ends 308 of the self-expanding mesh 300 ends can be secured to the proximal section 202 of a pre-shaped inner embolic element 200 while the inner embolic element 200 is in a substantially straight configuration (e.g. under tension) as shown in FIG. 12a. Once unconstrained, after deployment from the catheter 10, the self-expanding mesh 300 expands and foreshortens, as shown in FIG. 12b, creating internal space to allow for the pre-shaped inner embolic element 200 to take its predetermined expanded form. This allows for the inner embolic element 200 to shape the self-expanding mesh 300. The self-expanding mesh 300 can have a softness such that it allows for its shape to be modified by the stiffness of the inner embolic coil 200. In another example, the inner embolic element (coil) 200 can have a softness such that it allows for its shape to be modified by the stiffness of the self-expanding mesh 300 and conforms to the pre-shaped form of the self-expanding mesh 300. Thus, the proximal section 202 is shaped by the pre-determined shape of the mesh 300, and not necessarily pre-shaped itself.

Figure 13A:
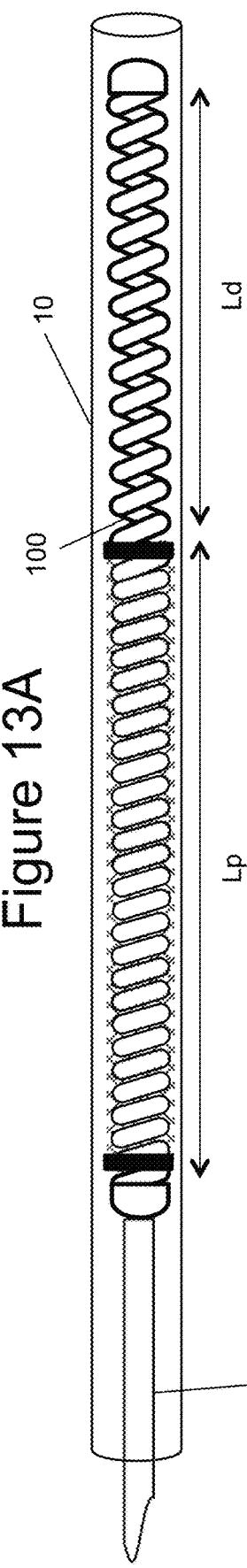
FIGS. 13a-13c illustrate an example of an embolic device being recaptured (i.e., pulled back into the catheter) after partial deployment from the catheter.
Figure 13B:
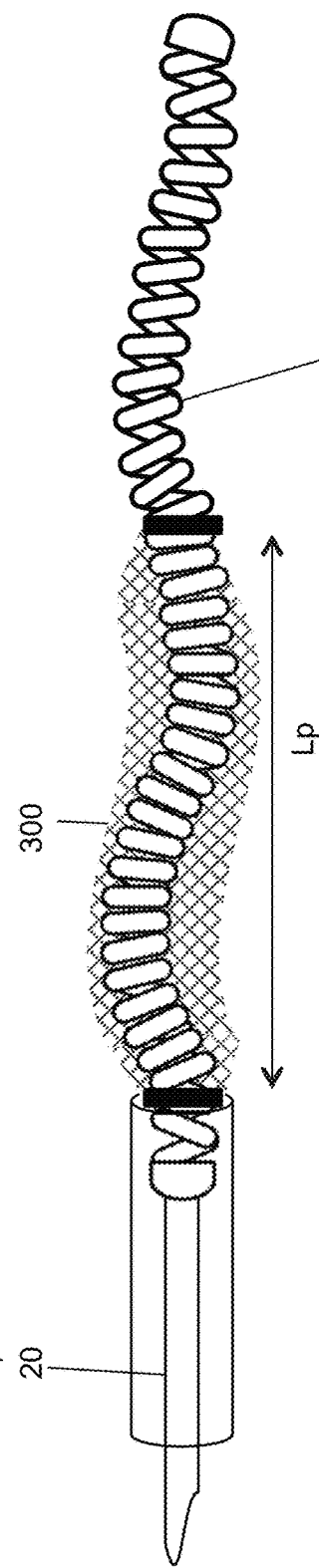
Figure 13C:
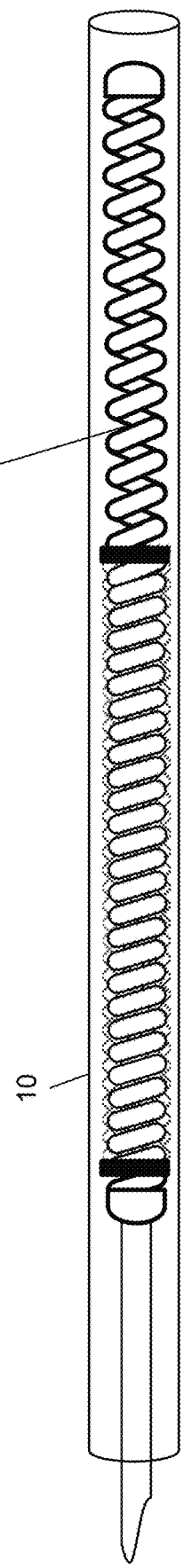

In other examples, the pre-shaping of the inner embolic element 200 and the expansion of the self-expanding mesh 300 are some the advantages to using the occlusion device 100 during a procedure. FIGS. 13a-13c illustrate that an occlusion device 100 can be deployed and retrieved akin to either a standard coil or mesh. FIG. 13a illustrates an occlusion device 100 connected to its delivery system 20 inside of a microcatheter 10. As the occlusion device 100 is pushed out of the microcatheter 10 the device 100 takes its predetermined expanded shape. The inner embolic element 200 begins to foreshorten and the mesh 300 begins to expand (FIG. 13b). However, before full deployment and release, the occlusion device 100 can be recaptured into the microcatheter 10, if desired (FIG. 13c).

FIGS. 13a-13c also illustrate the proximal section (Lp) in compression. The pitch of the coils differs from that of the distal section (Ld) so that the proximal section is in compression and wants to expand. This puts the mesh 300 in tension and it takes its collapsed state. This is illustrated in FIG. 13a. FIG. 13b illustrates the device 100 out of the catheter 10, which allows the proximal section (Lp) to decompress and take its preformed shape. At the same time the decompression removes the tension force from the mesh 300 to allow it to expand.

Turning back to the configuration of the mesh 300, FIG. 14 illustrates an example of a non-uniform configuration for the mesh 300 even while tensioned by the coil 200. So, the mesh 300 can be straight/tube like when tensioned over the inner embolic element (coil) 200 in the catheter 10. Other examples, the tensioned form of the mesh 300 can have a non-tube like shape. The mesh 300 can take any shape, with the caveat that the shape must be able to be disposed in, and translate through, the catheter 10. The inner embolic element 200 as well can have a pre-determined shape in the catheter 10 that is not straight, as long as it can be deployed. The shapes of the inner embolic element 200 and mesh 300 can be similar, different, or complimentary, that is to say that the mesh 300 and inner embolic element 200 may have different shapes, but the shapes support or enhance the packing density. The shapes can be in two or three dimensions.

In other examples, a mesh 300 can take even more complex configurations along with the underlying coil 200. FIG. 15 illustrates non-limiting examples of cross-sections for a mesh 300. The examples include (1) round, (2) elliptical and/or oval, (3) a stadium and/or capsule, (4) half-circle and/or circular cap, and (5) triangular. These are 2-dimensional descriptions of three dimensional shapes which can include spherical, spherical cap, hemispherical, ovoid, cylindrical, etc.

Figure 17A:
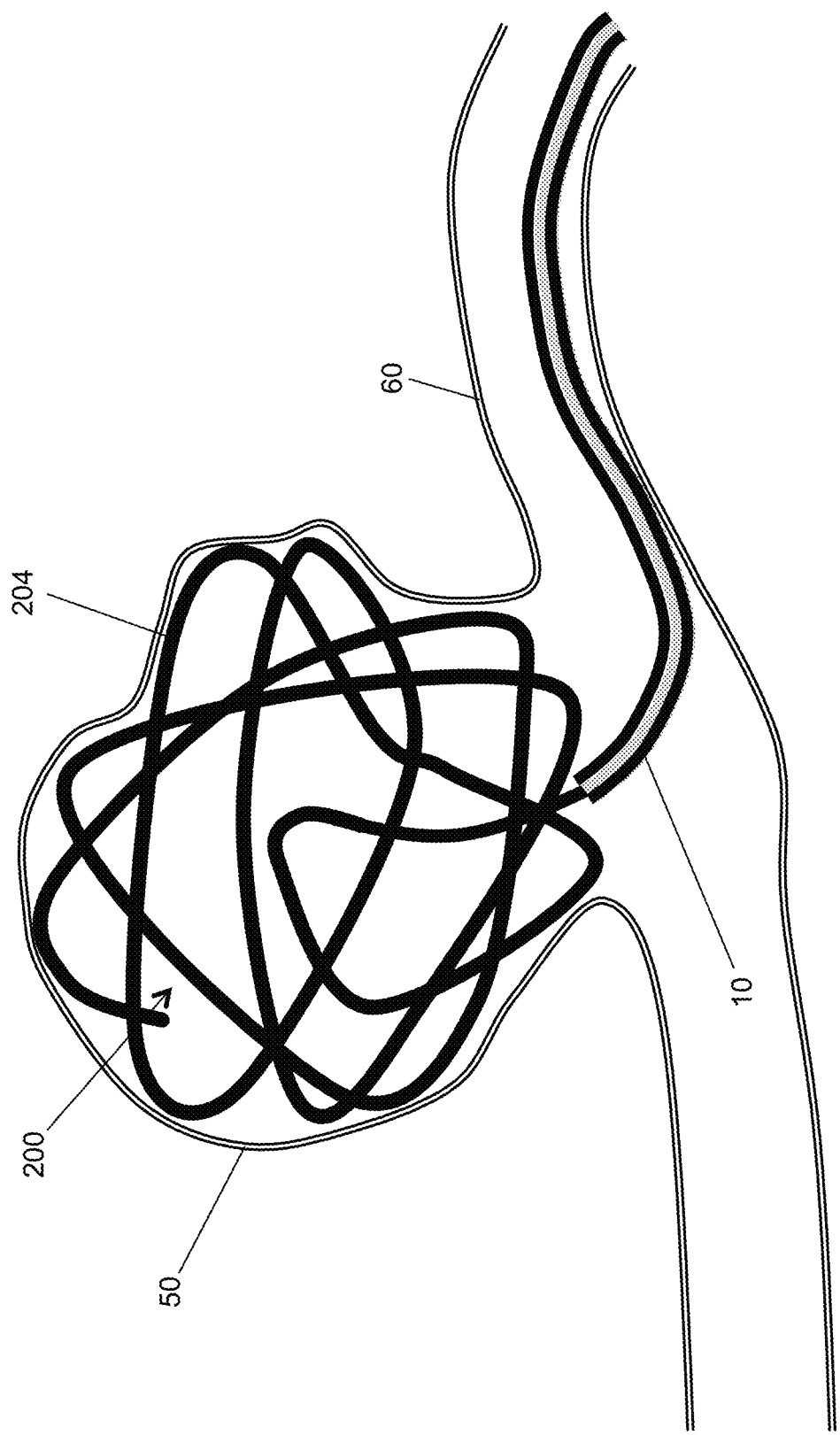
FIGS. 17a-17c illustrate the vascular occlusion device being deployed into an aneurysm.
Figure 17B:
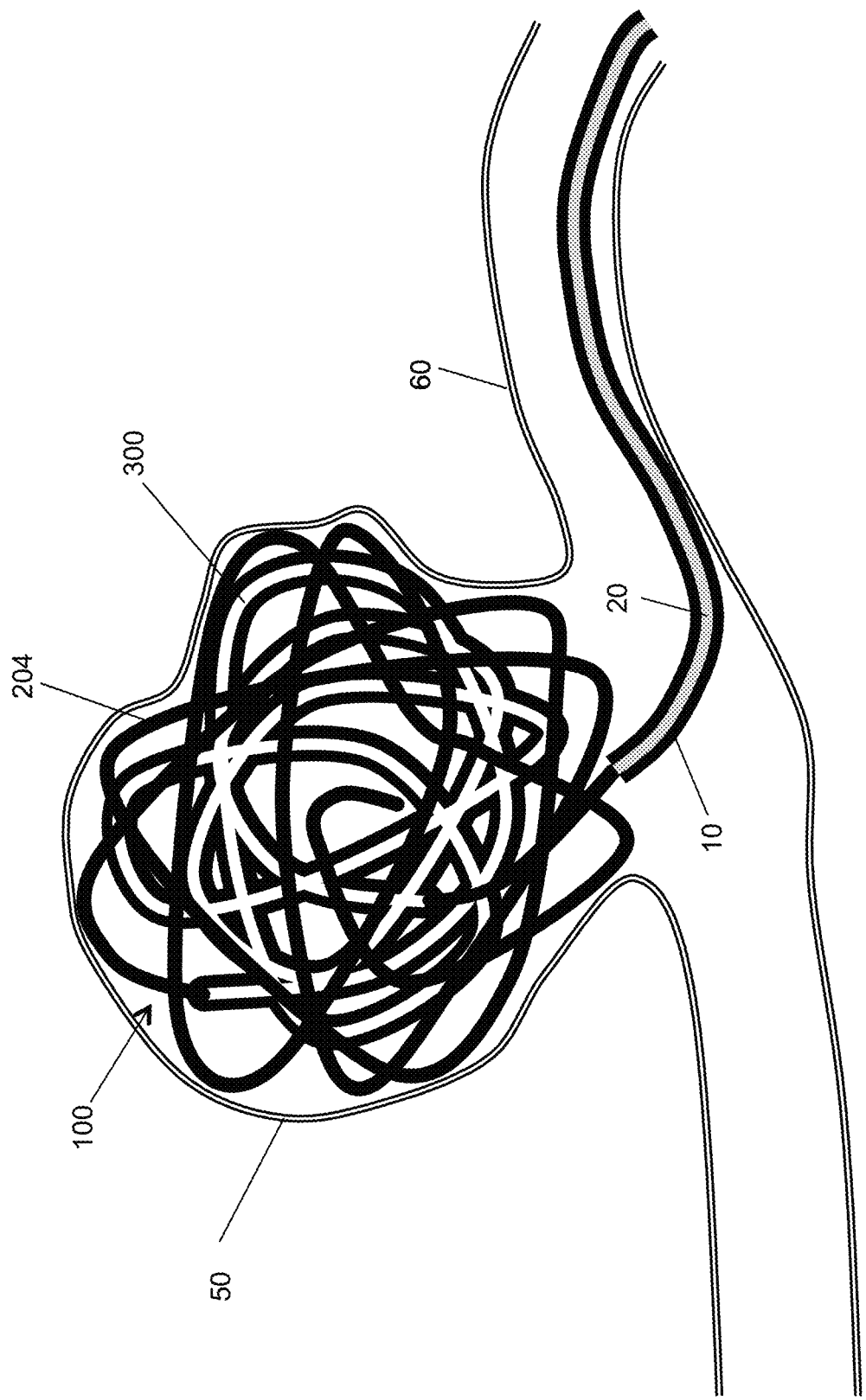
Figure 17C:
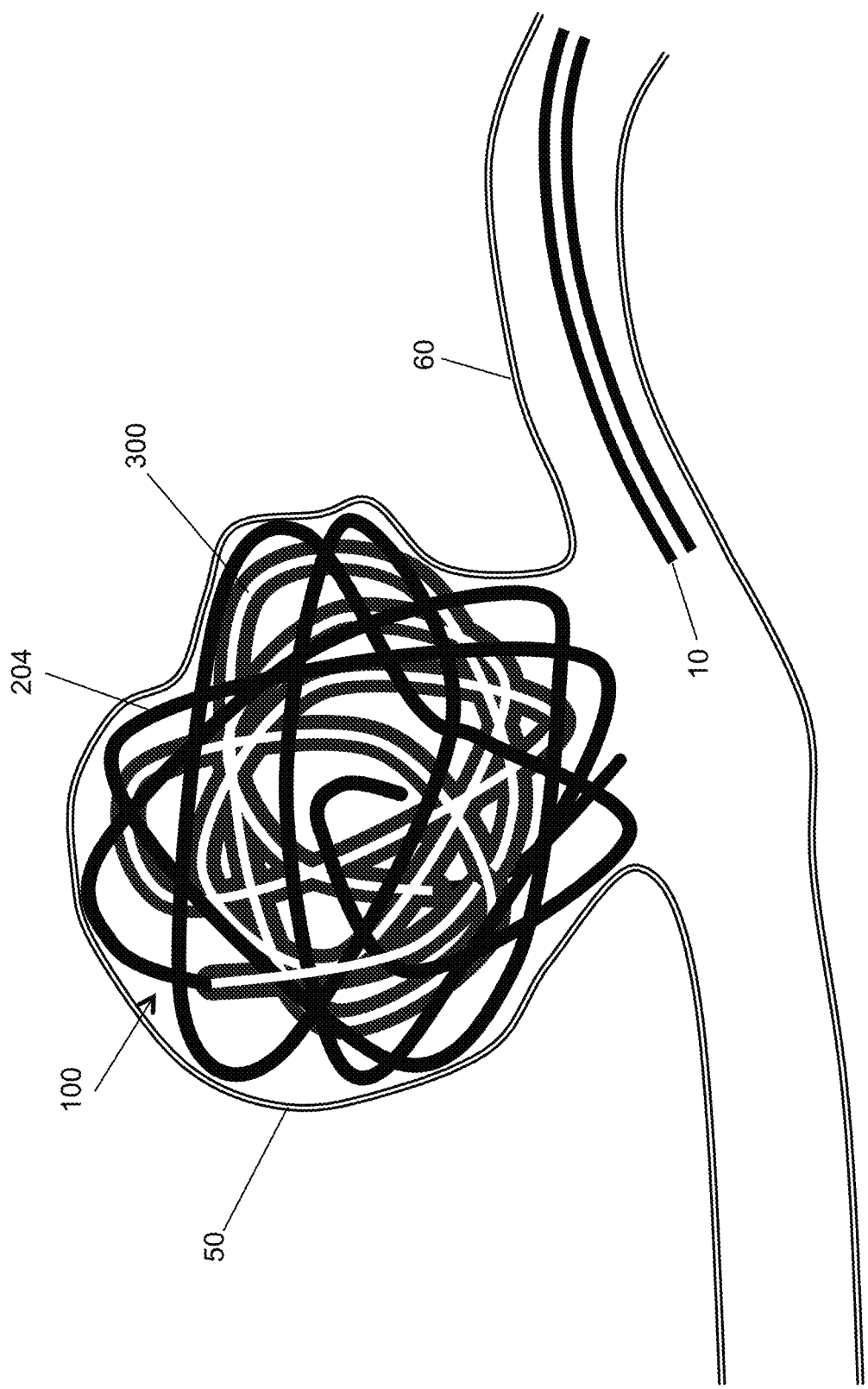

The examples of configurations of the inner embolic element, such as a coil, 200 and a mesh 300 result in the final shape of the occlusion device 100 once it is deployed from the catheter 10. FIGS. 16a and 16b illustrate the complex 3D shape the occlusion device 100 can form once full deployed. FIGS. 17a-17c illustrate the occlusion device 100 being deployed into an aneurysm 50. The catheter 10 has been delivered through a body lumen 60 to the aneurysm 50. In FIG. 17a, just the distal portion 204 of the inner embolic element 200 has been deployed from the catheter 10. The distal portion 204 can also be referred to as a framing coil portion of the inner embolic element 200. The framing coil 204 begins to take its predetermined shape and forms a structure that outlines and supports the walls of the aneurysm 50. After a length of the distal portion 204 is deployed, and in some examples, once the transition zone 206 is passed, the proximal portion 202, with the self-expanding mesh 300, begins to be deployed from the catheter by using the delivery member or other suitable technique.

FIG. 17b illustrates the majority of the occlusion device 100, both the inner embolic element, here shown as a coil 200 and a mesh 300, deployed out of the delivery catheter 10 and into the aneurysm 50. The device 100 takes the shape of the aneurysm 50 similar, but unlike prior art embolic coils, since it uses shorter coils and less coils. In addition, the mesh 300 provides more surface area for blood clots to form and create a thrombus. As the mesh 300 is deployed, it takes its predetermined shape and/or the shape imposed upon it by the proximal section 202 of the inner embolic element 200. The mesh 300 begins to "fill in" the structure formed by the framing coil, i.e. the distal, "unmeshed" end 204. Finally, once the position of the occlusion device 100 is satisfactory, the device 100 is detached from the delivery system 20 and left in the aneurysm 50, as illustrated in FIG. 17c. Using the inventive devices, surgeons may only need to use one device to achieve a satisfactory packing density without compaction, unlike prior art occlusion devices.

Figure 18:
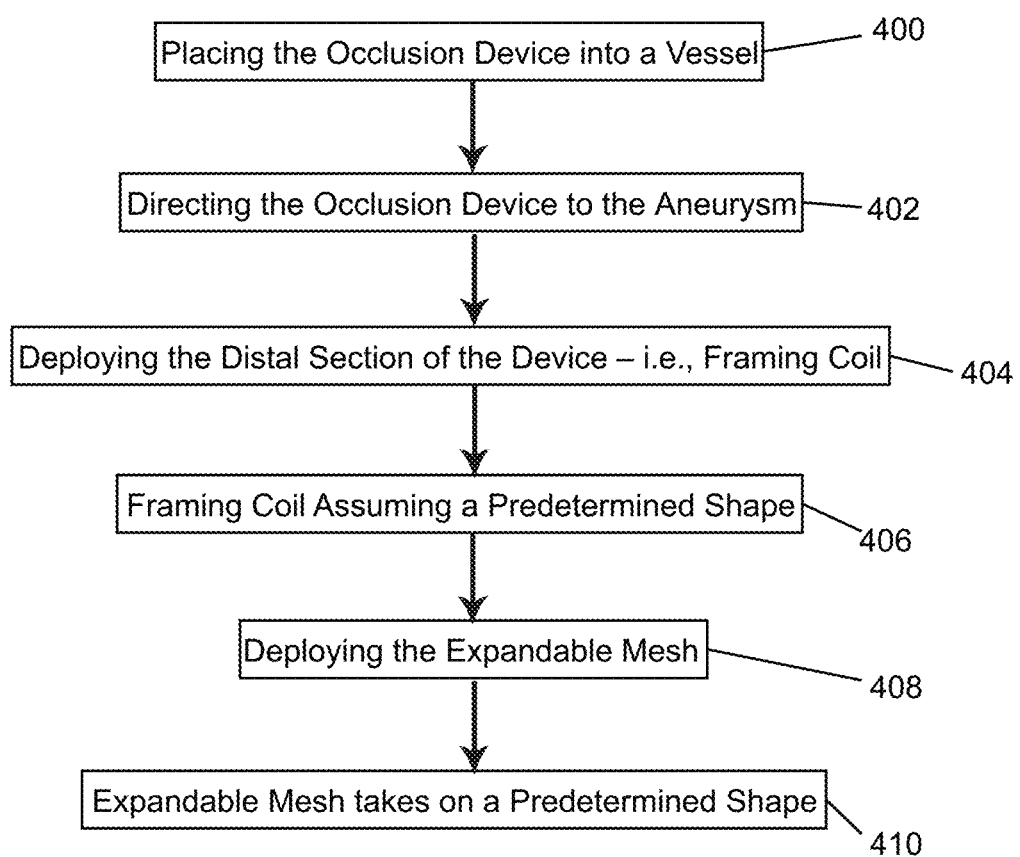
FIG. 18 is a flow chart of an exemplary method of the present invention.

FIG. 18 illustrates an example of a method of treating an aneurysm with an example of the present invention. The method includes using any of the examples of the occlusion device 100 having the inner embolic element, described here as a coil 200 and the expandable mesh 300, where the expandable mesh is disposed over a proximal part 202 of the inner embolic element 200. The distal part 204 of the inner embolic element 200 can be a framing coil. The occlusion device 100 is placed within a vessel or body lumen of a patient (step 400) and directed to the aneurysm (step 402). The distal portion/framing coil 204 is deployed into the aneurysm (step 404) and takes on its predetermined shape (step 406). Next, the expandable mesh 300 is deployed into the aneurysm, with the proximal part 202 of the inner embolic element 200 (step 408). The expandable mesh 300 takes on its expanded shape (step 410). Another example of the method can include a step of configuring or selecting different stiffnesses for the inner embolic element so that the framing coil/distal section is stiffer than the proximal section. For example, the stiffness can be determined in advance of the procedure using the example configurations as disclosed above or methods known to those of skill in the art. The surgeon can select the appropriately sized and stiffened occlusion device 100 for the needs of the patient at, or before, the time of the procedure.

FIGS. 19a and 19b provide a cross-section comparison of an intervention using an occlusion device 100 of the present invention and conventional coiling procedures with conventional embolic coils. In conventional procedures (top of FIG. 19a), a first coil, a framing coil 70, is deployed into the aneurysm. The framing coil 70 is typically the stiffest, or firmest, and frames a "cage" in the aneurysm. The framing coil 70 can be up to approximately 60 cm long. Additional coils, second coil 72, third coil 74, fourth coil 76, etc. are deployed into the aneurysm to continually fill the structure created by the framing coil 70 until the aneurysm is filled to a density to achieve thrombosis. The second, third, and fourth coils 72, 74, 76 are softer than the framing coil 70 and can get progressively softer with each successive coil. The successive coils 72, 74, 76 are generally softer to minimize the pressure against the walls of the aneurysm to minimize the chance of rupture. This conventional procedure typically requires 5-7 coils to achieve preferably greater than 25% packing density.

In contrast, FIG. 19b illustrates a mesh procedure using any of the examples of the occlusion device 100 of the present invention. Here, the distal section 204 of the inner embolic element 200 can act as a framing coil. The proximal section 202 of the inner embolic element 200 along with the self-expanding mesh 300 is deployed into the aneurysm and replaces the multiple coils used in the conventional procedure to fill the structure created by the framing coil. The embolic device 100 can reach over a 40% packing density with a single deployed device. This minimizes both surgical time and complexity, as multiple coils do not need to be individually deployed.

Figure 20A:
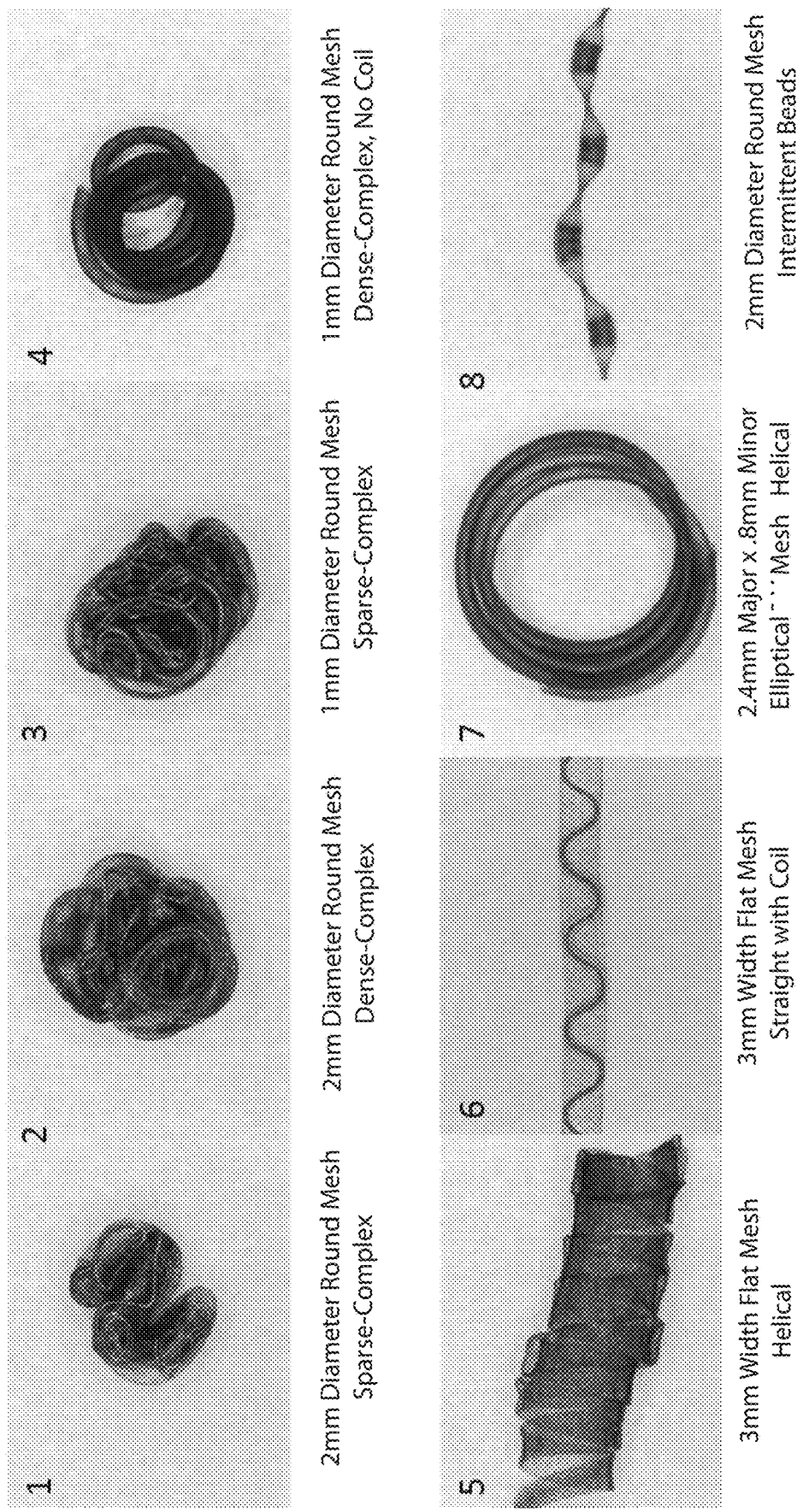
FIGS. 20a, 20d, and 20e illustrate multiple simple and complex shapes for a vascular occlusion device.

FIG. 20a illustrates examples of different shapes of deployed embolic devices 100 as follows: (1) 2 mm diameter round mesh, sparse packing, complex shape; (2) 2 mm diameter round mesh, dense packing, complex shape; (3) 1 mm diameter round mesh, sparse packing, complex shape; (4) 1 mm diameter round mesh, dense packing, complex shape, no coil; (5) 3 mm wide, flat mesh, helical shape; (6) 3 mm wide, flat mesh, straight shape, coil in inner embolic element; (7) 2.4 mm major axis×0.8 mm minor axis elliptical mesh, helical shape; and (8) 2 mm diameter round mesh formed with intermittent beads.

Figure 20C:
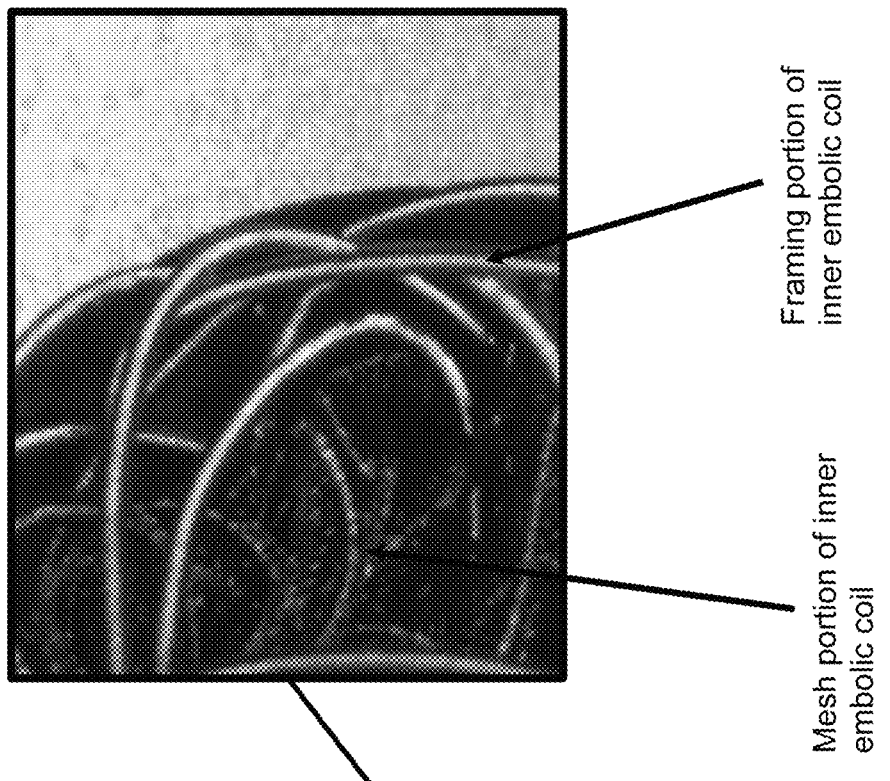
FIGS. 20b and 20c illustrate an example of a deployed vascular occlusion device and a magnified section thereof.
Figure 20B:
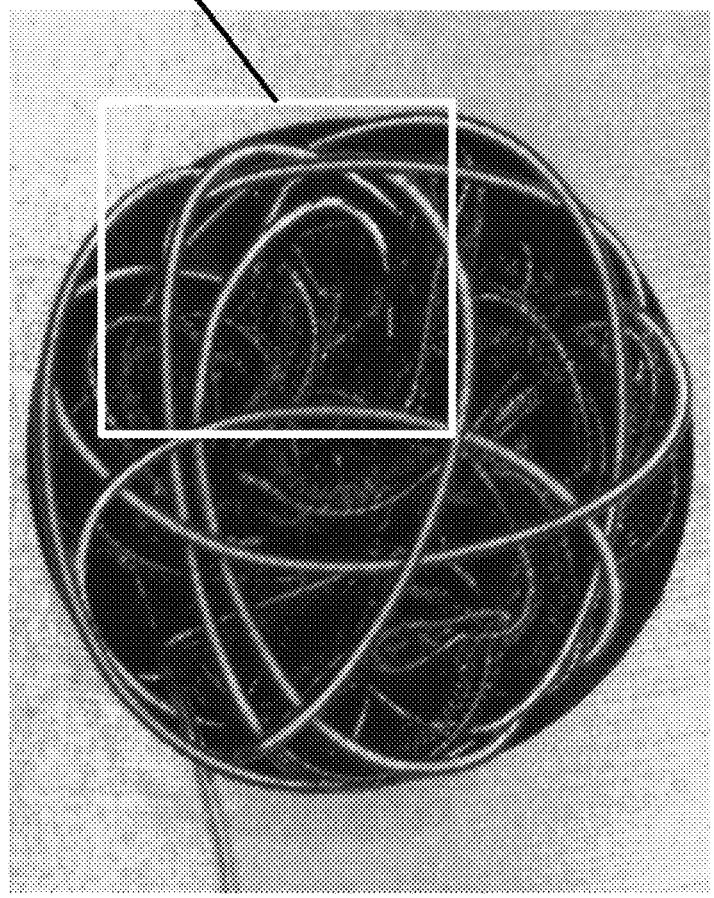
Figure 20D:
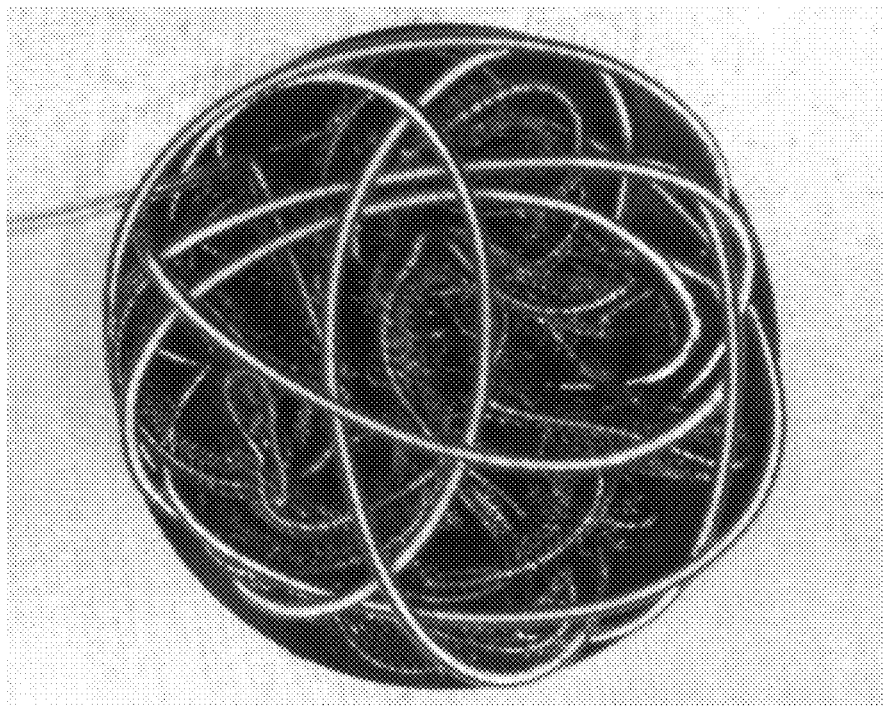
Figure 20E:
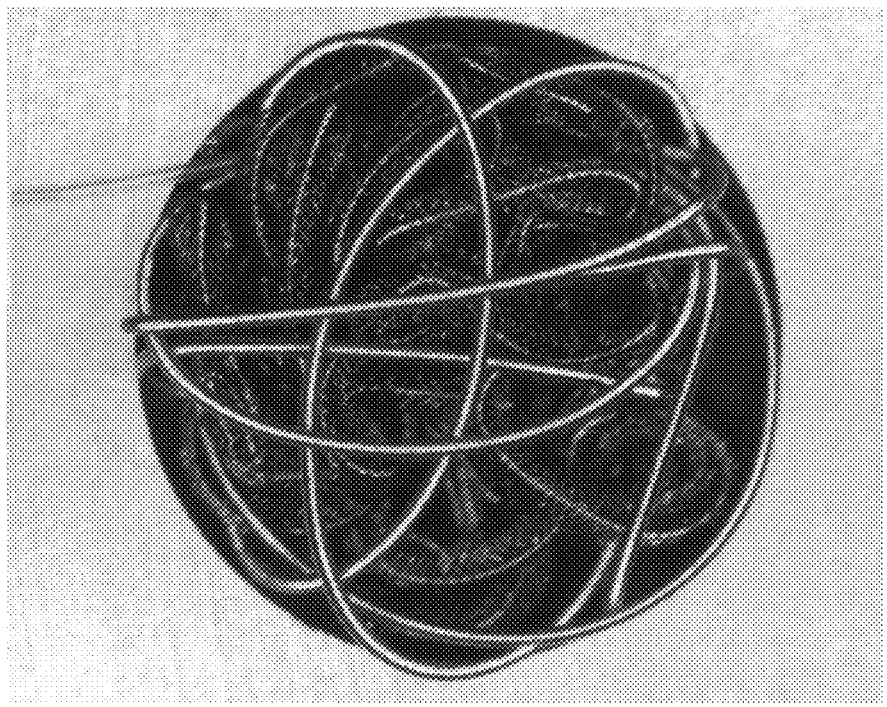

FIGS. 20b and 20c illustrate another example of a deployed occlusion device 100. FIG. 20c is a magnified section of the deployed device of FIG. 20b. Identified is the mesh portion over the inner embolic element 200, (i.e. the proximal section Lp with the mesh 300) and the framing portion of the inner embolic element 200, (i.e. the distal section Ld with embolic element 200). Here both are fully deployed and in FIG. 20c the mesh 300 is in its expanded state. FIGS. 20d and 20e are two other examples of the deployed vascular occlusion device of the invention.

FIG. 21 illustrates a number of example ratios of distal section lengths (Ld) vs. total device lengths (L). The calculations are for aneurysms ranging from 4 mm to 34 mm in diameter. Assumptions for the calculations are that the distal section 204 is to "frame" the aneurysm 50 and the proximal section 202 with the mesh 300 over it is to "pack" the aneurysm. FIG. 21 illustrates ratios for a length of the distal section Ld and a length of the deployed self-expanding mesh over the proximal section (see, FIGS. 7 and 10). The examples are considered idealized because of a number of assumptions, one is that the coil forms a 'spherical shell' of uniform thickness equal to the coil diameter (0.635 mm=0.025" and 0.2032 mm=0.008"), the outer diameter of the shell is equal to the aneurysm diameter and the hollow sphere the shell forms is packed with mesh to an equal packing density as the coil in the shell. In other examples, the mesh in the hollow sphere is packed at twice and 4 times the packing density as the coil in the shell. In these examples, packing density calculations assume the mesh maintains its unconstrained diameter during packing. Because meshes are compressible, unlike coils, it is possible to pack meshes to much higher packing densities than coils. These dimensions and calculations are intended to be illustrative and are in no way intended to limit the scope of the claimed invention.

Exemplary embodiments may have ratios between the Ld and the device length L total varying between 7% to 97.3%. Other ratio ranges can include between approximately 10% to approximately 23%, approximately 30% to approximately 45%, approximately 52% to approximately 69%, approximately 71% to approximately 85% and approximately 90% to approximately 97%.

In addition to the examples disclosed above, in which the framing coil is deployed into an aneurysm first as the distal section and the mesh follows along with the proximal section of the inner embolic element, the deployment order can be reversed. Thus, it is possible to deploy the proximal section of the inner embolic element carrying the mesh and then deploy the distal section, i.e. the framing coil. In an example of the reversed configuration, any or all of the other parameters discussed above can be utilized. Alternately, variations in the stiffness and lengths between the framing end and the braided end can be changed based on the nature of the deployment.

The descriptions contained herein are examples of embodiments of the invention and are not intended in any way to limit the scope of the invention. As described herein, the invention contemplates many variations and modifications of the inventive vascular occlusion device, with framing coil, including numerous inner embolic elements, coil configurations, numerous stiffness properties for the inner embolic element, numerous mesh configurations, numerous materials for the inner embolic element and mesh, and methods for delivering the same. Also, there are many possible variations in the materials and configurations of the release mechanism. These modifications would be apparent to those having ordinary skill in the art to which this invention relates and are intended to be within the scope of the claims which follow.

What is claimed is:

1. A method of treating an aneurysm using an occlusion device having an inner embolic element with a proximal section and a distal section, and an expandable mesh, comprising the steps of:
    providing a first stiffness for the distal section;
    providing a second stiffness for the proximal section different from the first stiffness;
    disposing the expandable mesh over a portion of the proximal section of the inner embolic element;
    placing the occlusion device within a vessel of a patient;
    directing the occlusion device to the aneurysm;
    deploying the distal section of the inner embolic element into the aneurysm from a catheter;
    assuming, by the distal section of the inner embolic element, a predetermined shape;
    permanently deploying the expandable mesh into the aneurysm.

2. The method of claim 1 wherein the distal section of the inner embolic element is a framing coil, and further comprising the step of configuring the different stiffness of inner embolic element so that the framing coil is stiffer than the proximal section.

3. The method of claim 1, wherein the distal section has a stiffness that is at least ten times the stiffness of the proximal section.

4. The method of claim 1, wherein the distal section has a stiffness that is up to twenty times stiffer than the proximal section.

5. The method of claim 1, wherein the distal section has a stiffness that is up to thirty times stiffer than the proximal section.

6. The method of claim 1, wherein the distal section has a length that is approximately at least 7% of a total length of the occlusion device.

7. The method of claim 1, wherein the expandable mesh has a mesh length in a collapsed position; and
    wherein the proximal section has a proximal length, that is approximately 2%-5% longer than the collapsed mesh length.

8. The method of claim 1, wherein the first stiffness of the distal section is softer than the second stiffness of the proximal section.

9. A method of treating an aneurysm using an occlusion device having an inner embolic element with a proximal section and a distal section, and an expandable mesh, wherein the expandable mesh is disposed over a portion of the distal section of the inner embolic element, and wherein the proximal section having a different stiffness than the distal section, comprising the steps of:
    placing the occlusion device within a vessel of a patient;
    directing the occlusion device to the aneurysm;
    deploying the expandable mesh with the distal section of the inner embolic element into the aneurysm from a catheter;
    assuming, by the expandable mesh, a predetermined shape;
    deploying the proximal section of the inner embolic element into the aneurysm from a catheter; and
    assuming, by the proximal section of the inner embolic element, a predetermined shape to frame the aneurysm.

* * * * *